(12) United States Patent
van der Burg-Koorevaar et al.

(10) Patent No.: US 7,785,824 B2
(45) Date of Patent: Aug. 31, 2010

(54) HYDROLYSED CASEIN PRODUCT COMPRISING TRIPEPTIDES IPP AND/OR VPP

(75) Inventors: Monique Cecilia van der Burg-Koorevaar, Vlaardingen (NL); RenéBernardus Draaisma, Vlaardingen (NL); Johannes Schalk, Vlaardingen (NL)

(73) Assignee: Conopco Inc., Englewood Cliffs, NJ (US)

( * ) Notice: Subject to any disclaimer, the term of this patent is extended or adjusted under 35 U.S.C. 154(b) by 0 days.

(21) Appl. No.: 10/555,633

(22) PCT Filed: Apr. 23, 2004

(86) PCT No.: PCT/EP2004/004385

§ 371 (c)(1),
(2), (4) Date: Nov. 4, 2005

(87) PCT Pub. No.: WO2004/098309

PCT Pub. Date: Nov. 18, 2004

(65) Prior Publication Data

US 2007/0054352 A1   Mar. 8, 2007

(30) Foreign Application Priority Data

May 5, 2003   (EP) .................................. 03076307

(51) Int. Cl.
*C12P 21/06*   (2006.01)
*C12N 9/62*   (2006.01)
*A61K 35/20*   (2006.01)

(52) U.S. Cl. ........................ 435/68.1; 435/41; 435/225; 435/913; 435/918; 514/773; 514/775

(58) Field of Classification Search ........................ None
See application file for complete search history.

(56) References Cited

U.S. PATENT DOCUMENTS 6,994,987 B1 * 2/2006 Yamamoto et al. ......... 435/68.1

FOREIGN PATENT DOCUMENTS

| EP | 1016709 A1 | 7/2000 |
|---|---|---|
| EP | 1018341 A1 | 7/2000 |
| EP | 1 201 679 A2 | 5/2002 |
| EP | 1231279 A1 | 8/2002 |
| JP | 02036127 | * 2/1990 |
| JP | 02036127 A | * 2/1990 |
| JP | 10212245 | * 8/1998 |
| JP | 10212245 A | * 8/1998 |
| WO | WO 94/25580 | 11/1994 |
| WO | WO 96/13174 | 5/1996 |
| WO | WO 01/32836 A1 | 5/2001 |
| WO | WO 01/34828 A1 | 5/2001 |
| WO | WO 2004/060073 A1 | 7/2004 |
| WO | WO 2006/005757 A2 | 1/2006 |
| WO | WO 2006/067163 A2 | 6/2006 |
| WO | WO 2006/084573 A1 | 8/2006 |
| WO | WO 2006/089921 A1 | 8/2006 |
| WO | WO 2006/114192 A1 | 11/2006 |
| WO | WO 2006/114193 A1 | 11/2006 |
| WO | WO 2006/114194 A1 | 11/2006 |
| WO | WO 2006/114195 A1 | 11/2006 |
| WO | WO 2006/114439 A2 | 11/2006 |
| WO | WO 2006/114441 A1 | 11/2006 |

OTHER PUBLICATIONS

Greenberg, R., et al "Human b-Casein: Amino Acid Identification of Phosphorylation Sites" The Journal of Biological Chemistry. 1984, 259(8), 5132-5138.*
European Search Report Application No. 03076307.2-1221—mailed Oct. 23, 2003.
PCT International Search Report Application No. PCT/EP2004/004385 mailed Sep. 2, 2004.
Chiang W-D et al: "Casein Hydrolysate Produced Using a Formed-in-Place Membrane Reactor"; Journal of Food Science, Institute of Food Technologists, Chicago, U.S., vol. 60. No. 6. Nov. 1, 1995, pp. 1349-1352.
Bouchier et al: "*Hydrolysis of alphas1- and beta-casein-derived peptides with a broad specificity aminopeptidase and praline specific aminopeptidases from Lactococcus lactis subsp, Cremorls AM2*" FEBS Letters, Elsevier Science Publishers, Amsterdam, NL, vol. 445, No. 2-3, Feb. 26, 1999, pp. 321-324.
Byun et al: "*Synergetic Action of an X-Prolyl Dipeptidyl Aminopeptidase and a Non-Specific Aminopeptidase in Protein Hydrolysis*", Journal of Agricultural and Food Chemistry, American Chemical Society. Washington, US, vol. 49, No. 4, 2001, pp. 2061-2063.
Hata et al: "*A Placebo-controlled Study of the Effect of Sour Milk on Blood Pressure in Hypertensive Subjects*" The American journal of Clinical Nutrition. U. S., Nov. 1996, vol. 64, No. 5, Nov. 1996, pp. 767-771.
Database WPI, Section Ch, Week 200338, Derwent Publications ltd., London, GB; AN 2003-399727 XP002256819 & KR 2003 003 462 A (Rural Dev Administration), Jan. 10, 2003 , abstract.
Database FSTA Online! International Food Information Service (IFIS), Frankfurt/Main, DE; 1985, Takase et al: "*Use of Casein Hydrolysate in Special Foods*,". XP002256818, Database accession No. 85-1-07-g0013 abstract & Japanese Journal of Dairy and Food Science (Rakuno Kagaku Shokuhin No Kenkyu)) 1984 Cent. Res. Lab., Morinaga Milk Ind, Co. Ltd., 4-4-22 Meguro, Meguro-Ku, Tokyo, Japan, vol. 33, No. 1, 1984, pp. A5-Al2.
Guerard et al: "*Production of Tuna Waste Hydrolysates by a Commercial Neutral Protease Preparation*", Journal of Molecular Catalysis B Enzymatic, No. 19-20, Dec. 2, 2002, pp. 489-498.

(Continued)

*Primary Examiner*—Christopher R Tate
*Assistant Examiner*—Aaron J Kosar
(74) *Attorney, Agent, or Firm*—Morgan, Lewis & Bockius LLP

(57) ABSTRACT

Process for the preparation of a hydrolysed casein product comprising tripeptides VPP, IPP and/or LPP, wherein a substrate comprising casein or casein fragments is subjected to enzyme treatment wherein the enzyme is derived from *Aspergillus*, wherein the enzyme concentration is 2-10 wt. % based on casein and that the enzyme has a high proteolytic activity.

4 Claims, No Drawings

OTHER PUBLICATIONS

Tachi et al: *An X-Prolyl Dipeptidyl-Aminopeptidase from Aspergillus Oryzae*, Phytochemistry, Pergamon Press, GB, vol. 31, No. 11, 1992, pp. 3707-3709.

Gerstein et al. (2000), The Lancet 355, 253-259.

Kunji et al., (1998), Molecular Microbiology 27, 1107-1118.

Christensen et al., (1999), *Int. Journal of Gen. & Molecular Microbiology* 76, 217-246.

Kohmura at al. (1990), Agricultural and Biochemical Chemistry, 54, 835-836.

Nakamura et al. (1995) J. Dairy Sci. 78, 1253-1257.

Maruyama et al (1989), Agricultural and Biochemical Chemistry, 53, 1077-1081.

Miyoshi at al, (1991), Agric. Biol. 55(5), 1407-1408.

Adler-Nissen, J. Agric. Food Chem., vol. 27. No. 6, 1256-1262 (1979).

Adler-Nissen, J., Enzymatic Hydrolysis of Food Proteins, New York: Elsevier Applied Science Publishers. p. 110-169 (1986).

Smyth, et al, "Relationship between Some Characteristics of WPC Hydrolysates & the Enzyme Complement in Commercially Available Proteinase . . . ", Preparations Int. Dairy. Journal, 1998, 8(9), pp. 819-827.

* cited by examiner

HYDROLYSED CASEIN PRODUCT COMPRISING TRIPEPTIDES IPP AND/OR VPP

FIELD OF THE INVENTION

The invention relates to a hydrolysed casein product comprising tripeptides VPP, IPP and/or LPP. The invention further relates to a process for the preparation of such hydrolysed casein product and to food products produced using the hydrolysed casein product.

BACKGROUND TO THE INVENTION

Hypertension or high blood pressure is considered to be one of the main risk factors for Cardio Vascular Diseases (CVD). One of the mechanisms which regulates blood pressure is the renin-angiotensin system. This is a cascade of reactions leading to the formation of angiotensin II, which has a strong vasoconstrictive and hence blood pressure increasing effect. Inhibition of one of the key enzymes in this cascade: Angiotensin I Converting Enzyme (ACE) reduces formation of angiotensin II and thus has a blood pressure lowering effect. Long term human intervention studies have shown regular intake of low amounts of ACE inhibitors reduces CVD by 25% (Gerstein et al. (2000), The Lancet 355, 253-259).

In a placebo-controlled study, the blood pressure lowering effect of VPP and IPP in sour milk was shown in hypertensive humans (Hata, Y et al. (1996), American Journal of Clinical Nutrition 64, 767-771).

A commercially available fermented milk product, which claims to be "suitable for those with mild hypertension" is Calpis sour milk, fermented with *Lactobacillus helveticus* and *Saccharomyces cervisiae*, produced by Calpis Food Industry, Japan.

Another commercially available fermented milk product is Evolus produced by Valio, Finland, which claims to be 'the first European functional food to help lower blood pressure'.

Both fermented milk products are fermented with *Lactobacillus helveticus* (*Lb. helveticus*) strains. The products contain bioactive peptides (VPP and IPP) responsible for in vitro ACE inhibition, which are produced by proteolysis of caseins. Compared to other lactic acid bacteria *Lb. helveticus* is one of the most efficient proteolytic *Lactobacillus* species.

The breakdown of caseins by the proteolytic system of lactic acid bacteria can be divided into three stages. Initially breakdown of casein is performed by extracellular proteinases, followed by the uptake of di/tri peptides and oligopeptides (4 to 12 amino acidic residues) using specific uptake mechanisms. In the last stage, peptides are further degraded by intracellular peptidases, yielding small peptides and amino acids for bacterial growth. This complicated proteolytic system of lactic acid bacteria is described in Kunji et al., (1996), Molecular Microbiology 27, 1107-1118. A review on the intracellular peptidase system can be found in Christensen et al., (1999), Molecular Microbiology 76, 217-246.

According to EP-A-1016709, it is desired to produce fermented milk with higher content of the lactotripeptides compared to the content of the lactic acid generated in the fermented milk. It provides a *Lactobacillus helveticus* strain CM4 that in fermentation gives 30-50 μg of tripeptides Val-Pro-Pro (VPP) and Ile-Pro-Pro (IPP) per 0.01 g of DL-lactic acid. In table 2 of EP-A-1016709 it is shown that this strain produced 38.5 μg/ml whey of VPP and 23.5 μg/ml whey IPP, which corresponds to an IPPeq value, as defined hereinafter, of 140.

WO 01/034828 discloses a process for producing tripeptides VPP and/or IPP starting from casein using enzymes. In the process casein is treated with proteinase to produce an intermediate peptide and then digesting the intermediate peptide with peptidase. The best results in WO 01/034828 are shown in example 2 where casein hydrolysed with papain and *Lactobacillus helveticus* derived peptidase gives a VPP yield is 25% and the IPP yield 97.5%, based on beta-casein. Assuming an average content of 30 wt. % beta-casein and 15 wt. % kappa-casein in skim milk powder, the yield of IPP yield of 97.5% based on beta-casein corresponds to a yield of 54% based on beta-casein and kappa casein together, as used herein. In the other examples lower yields are reported.

SUMMARY OF THE INVENTION

It is an object of the invention to provide a food product having a high content of tripeptides VPP, IPP and/or LPP. In view of WO01/034828 it is an object to increase the yield of the tripeptides VPP and/or IPP. It is another object to provide a process for the preparation of a food product comprising VPP, IPP and/or LPP that is simple and low cost. Another object is to provide a food product having a good taste.

One or more of these objects are attained according to the invention, which provides a process for the preparation of a hydrolysed casein product comprising tripeptides VPP, IPP and/or LPP, wherein a substrate comprising casein or casein fragments is subjected to enzyme treatment wherein the enzyme is derived from *Aspergillus*, wherein the enzyme concentration is 2-10 wt. % based on casein and that the enzyme has a high proteolytic activity.

According to a preferred embodiment the enzyme comprises endopeptidases, exopeptidases and proteinases.

The invention further relates to a hydrolysed casein food product comprising 200 μM or more of IPPeq, preferably 400 μM or more of IPPeq as defined hereafter. Advantageously the hydrolysed casein food product has a non-bitter taste.

DETAILED DESCRIPTION OF THE INVENTION

The weight percentages herein will be expressed relative to the total weight, unless otherwise indicated.

Enzyme is herein understood to also include a mixture of more than one enzyme.

The common one letter code is ordinarily used to describe amino acids.

Casein is herein understood to include all types of casein, including alpha casein, beta casein, gamma casein and kappa casein. It is noted that the fragment IPP occurs in both beta- and kappa-casein. The fragments VPP and LPP both occur once in beta casein.

Substrate herein means any material containing casein and/or casein fragments, when used as the material treated with the enzyme.

Proteases are herein any of a group of enzymes that cleave peptide bonds of proteins (polypeptides) resulting in shorter peptides and amino acids.

Exopeptidase is herein defined as an enzyme that acts only near the ends of polypeptide chains. Based on their site of action at the N or C terminus they are classified as amino- or carboxypeptidases, respectively.

Endopeptidase is herein defined as an enzyme that acts preferentially at the peptide bonds in the inner regions of the polypeptide chains away from the N and C termini.

High proteolytic activity of the enzyme is herein defined as a proteolytic activity corresponding to a degree of hydrolysis of 20% or higher as measured in accordance with the experimental part of this specification, at a hydrolysis time of 6 hours and en enzyme concentration of 5 wt. % based on casein.

Preferably the enzyme has a X-Prolyl dipeptidyl aminopeptidase activity or 400 U/kg or more, more preferably 700 U/kg or more, even more preferably 1200 u/kg or more.

The peptide Val-Pro-Pro is abbreviated as VPP; the peptide Ile-Pro-Pro as IPP and Leu-Pro-Pro as LPP. *Lactobacillus* is herein abbreviated as Lb.

Tripeptides VPP, IPP and/or LPP as defined herein include VPP, IPP, LPP and mixtures of these peptides. The total molar amount of tripeptides VPP, IPP and/or LPP in mixtures are herein calculated by addition of molar amounts of the tripeptides in the mixture.

The process according to the invention produces the active tripeptides VPP, IPP, and LPP, which have a different activity. The $IC_{50}$, the concentration which results in 50% inhibition of the ACE activity is 5 µM for IPP and 9 µM for VPP (Kohmura, M. et al. (1990), Agricultrural and Biochemical Chemistry, 54, 835-836 and Nakamura, Y et al. (1995), J. Dairy Sci. 78, 1253-1257). The $IC_{50}$ ACE inhibition value for LPP is 9.6 µM (Maruyama S. et al. (1989), Agricultural and Biochemical Chemistry, 53, 1077-1081). LPP was shown to be present in a maize (zein) hydrolysate, which had an antihypertensive effect in spontaneously hypertensive rats (M. Shinsuke et al (1991), Agric. Biol. 55(5), 1407-1408).

To express the overall concentration of these active peptides IPP and VPP in a single FIGURE, the equivalent IPP concentration [IPPeq] is used herein, which is defined as follows and preferably expressed in µM:

$$[IPPeq] = [IPP] + 5/9*[VPP] \quad (1)$$

To express the overall concentration of all active tripeptides containing a branched chain amino acid -Proline-Proline sequence e.g. IPP, VPP and LPP, the equivalent BPP concentration (BPPeq) is also used herein, which is defined as follows and expressed in µM:

$$BPPeq = [IPP] + 5/9*[VPP] + 5/9.6*[LPP] \quad (2)$$

The process according to the invention involves a step in which a substrate is subjected to treatment with an *Aspergillus* derived enzyme. Substrate is herein defined as the material that is subjected to the enzyme treatment.

The substrate may be any casein and/or casein fragment containing material suitable as the basis for human food.

Preferably the substrate is milk. Animal milk such as cow's milk, goat's milk, camel milk, horse's milk, may be used as substrate. Skim milks may be used. The content of the solid in the substrate is not particularly limited, but is usually 5 to 20 wt %. The substrate may be reconstituted milk, prepared by mixing water and milk ingredients, for instance (skim) milk powder. The substrate may contain additives, such as carbohydrates, etc. as long as these additives do not interfere with the enzyme treatment and/or fermentation.

Preferably caseinates, such as for instance potassium-caseinate and/or calcium caseinate may be used in a substrate.

In a preferred embodiment the substrate is fermented milk which may be produced according to the fermentation process described hereinafter. In this preferred embodiment casein is first subjected to fermentation and thereafter to enzyme treatment.

Another embodiment involves that fermentation and enzyme treatment are conducted simultaneously, e.g. by adding the *Aspergillus* derived enzyme to the fermentor in which the fermentation takes place.

The enzyme treatment may be done in a conventional manner. It involves adding enzyme (or a mixture of enzymes) to the substrate and maintaining the resulting reaction mixture under controlled conditions suitable for conducting the enzymatic hydrolysis. The conditions to be controlled include temperature, pH, reaction time and enzyme concentration. The preferred temperature of the reaction mixture is 40-60 degrees C., more preferred 45-55 degrees C. and most preferred about 50 degrees C. The pH of the reaction mixture is preferably 5 to 9, more preferably 5.5 to 7 and most preferably 6 to 6.5. The enzyme concentration is 2-10 wt. % based on the total weight of the casein, more preferably 3-10 and most preferably 4-6 wt %. The reaction time (hydrolysis time) is preferably 2-50 hours, more preferably 2-10 hours and most preferably 4-8 hours. The enzyme should be derived from *Aspergillus*. We have surprisingly found that conducting hydrolysis of casein with a relatively high amount of enzyme derived from *Aspergillus* results in much higher amounts of the tripeptides VPP, IPP and/or LPP. Preferably the enzyme is derived from *Aspergillus oryzae*.

In another preferred embodiment the hydrolysis of casein may be substituted by a fermentation step with *Aspergillus*. In this preferred embodiment it is believed that the fungus *Aspergillus* will during fermentation produce the enzymes that cause hydrolysis of the casein in situ. In this preferred embodiment the fermentation should be conducted in such way that high amounts of enzymes (including endopeptidase, exopeptidase and proteinase) are produced in situ.

Food products according to the invention are defined as products, suitable for human consumption, in which a casein hydrolysis product according to the invention was used as an ingredient in an effective amount, such that a noticeable ACE-inhibitory effect is obtained.

DESCRIPTION OF A PREFERRED EMBODIMENT INVOLVING FERMENTATION

According to this preferred embodiment the substrate for the enzyme treatment is a fermentation product resulting from *Lb. helveticus* fermentation. The process for preparing the hydrolysed casein product therefore optionally involves a fermentation step.

The *Lb. helveticus* fermentation may be executed in conventional fermentors, in which casein containing starting material as a medium is inoculated with the *Lb. helveticus*. The casein containing starting material may be any material containing casein and is preferably a material that may also be used as substrate as defined hereabove, e.g. milk.

The conditions of the fermentation step are specified below. The *Lb. helveticus* may be any *Lb. helveticus* strain. Preferred are those strain that produce high amounts of tripeptide VPP and/or IPP. Most preferred is *Lactobacillus helveticus* strain CNRZ 244, deposited at Centre National de Recherches Zootechniques, Jouy-en-Josas, France.

Other microorganisms may optionally be added to the fermentation medium as long as the object of the present invention is achieved. For example, yeast may additionally be used for improving the flavour and palatability of the resulting hydrolysed casein product.

Strains of the yeast are not particularly limited, and for example, yeast of the genus *Saccharomyces* such as *Saccharomyces cerevisiae* may preferably be used. The content of the yeast may suitably be selected, depending on the desired result.

There is no particular limitation on the amount of the *Lb. helveticus* with which the medium is inoculated. The inoculation amount is usually about $10^7$ to $10^9$ cells of the *Lb. helveticus* bacteria.

The *Lb. helveticus* may be added to the fermentation preferably in the form of a precultured starter having sufficient activity. The initial cell count of the starter is preferably about $10^7$ to $10^9$ cells/ml.

The materials in the fermentor, including *Lb. helveticus* inoculum and the casein containing starting material, may be mixed in conventional way, in order to achieve a homogeneous fermentation medium.

The fermentation advantageously may be performed at 25 to 50° C. and preferably 35 to 45° C., for 3 to 80 hours and preferably 6 to 25 hours. Preferably the fermentation temperature is 38-42° C., since in this temperature range the highest amount of tripeptides VPP and/or IPP is formed.

The pH during fermentation is critical as to the amount of tripeptides VPP and/or IPP formed. Preferably therefore, the pH during a substantial part of the fermentation is 4.3-4.9, more preferably 4.4-4.8 and most preferably 4.5-4.7. A substantial part of the fermentation means in this context at least 1 hour or more of the fermentation time. Preferably the pH of during fermentation is controlled during 3 hours or more of the fermentation time, more preferably 5 hours or more.

The pH may be controlled by addition of base (or buffer) to the fermentation medium. The base may be any base suitable for use in the preparation of food products. Such controlled fermentation is herein called pH-controlled fermentation. Without pH-control is herein called free acidification fermentation.

During the fermentation, *Lb. helveticus* produces amongst others lactic acid. Lactic acid (HLa or LaH) dissociates into a proton, $H^+$, and a lactate anion, La-(sometimes referred to herein as dissolved lactate salt when another source of cation is present, typically from the base or buffer salt). The amount of dissociation is related to the pH of the solution and the PKa of lactic acid. The pKa of lactic acid at 25° C. is 3.86 (at 50° C. it is about 3.89). Equation (2) below describes how the pH, pKa, and degree of lactic acid dissociation are related.

$$pH=pK_a+\log([La^-]/[LaH])  \quad (3)$$

Equation (2) shows that half the acid is dissociated when the pH equals the pKa of the acid. At higher pH values, the majority of the lactic acid is in the lactate anion form. If the fermentation broth has a pH value between 3.0 and 4.5, there will be a significant amount of lactic acid in the undissociated form. Indeed at a pH of 3.0 the molar ratio of free lactic acid (undissociated) to lactate ion at 25° C. is about 7.0; and, at a pH of about 4.5 the ratio at 25° C., is about 0.23.

A preferred protocol for pH-controlled fermentation is executed as follows: After inoculation (1) a free acidification fermentation until the desired pH is reached (in range 4.3-4.9), subsequently (2) a pH-controlled fermentation and optionally (3) subsequently a second free acidification fermentation until the termination, e.g. at pH 3.5-4.0. As result of this protocol a high amount of equivalent IPP can be produced, while maintaining a relatively low level of salts in the hydrolysed casein product.

Preferably the base is a metal salt, the metal of which is common in food, but does not increase the blood pressure. Preferably the base is a hydroxide. A base containing sodium, such as sodium hydroxide, is therefore preferably excluded. More preferably the base is a salt chosen from the group consisting of calcium salt, potassium salt and/or magnesium salt. The metal ions of such a base $K^+$, $Ca^{2+}$ and/or $Mg^{2+}$, which as a result of the pH-controlled fermentation will become part of the hydrolysed casein product, may decrease the blood pressure in humans.

Preferably the level of dissolved oxygen ($dO_2$) during fermentation is 5% or less. At low dissolved oxygen levels the production of tripeptides VPP and/or IPP is increased, compared to higher oxygen levels. The fermentor may be sparged with an inert gas, such as nitrogen in order to accomplish low dissolved oxygen levels.

Advantageously, after enzyme treatment and optional fermentation, several additional process steps may be executed. For instance, solid calcium lactate and/or magnesium lactate may be separated from the hydrolysed casein, e.g. by cooling the hydrolysed casein product, such that these lactates precipitate. The hydrolysed casein product may be used as such, or may be diluted, it may be concentrated, it may be purified and it may be dried, preferably spray-dried or freeze-dried. The dried hydrolysed casein product is hereafter also designated as hydrolysed casein solids.

According to the invention a relatively high number of VPP, IPP and/or LPP molecules may be liberated from the substrate. Preferably, the molar yield of VPP on its substrate is 30% or more, preferably 40% or more and more preferably 50% or more.

The molar yield of VPP is defined as the molar amount of VPP produced in the experiments (fermentation and/or enzymatic hydrolysis) divided by the molar amount of VPP fragments in the total mass of beta-casein present in the casein containing starting material prior to the start of the experiments. An analogous calculation gives the molar yield of IPP and LPP. Note that the VPP and the LPP sequence are present in beta-casein, while the IPP sequence is present in both beta- and kappa-casein.

The molar yield of IPP is preferably 60% or more, more preferably 75% or more and most preferably 80% or more.

With the process of the invention, a hydrolysed casein product is obtainable, which comprises an amount of tripeptides VPP, IPP and/or LPP expressed as equivalent IPP concentration [IPPeq] of 200 µM or more, more preferably 400 µM or more, even more preferably 600 µM or more and most preferably 700 to 3500 µM.

Preferably, in the process for the preparation of the hydrolysed casein product according to the invention, the molar yield of LPP is 20% or more, more preferably 45% or more, even more preferably 80% or more. Preferably the food products according to the invention comprise 25 µM or more LPP.

Preferably, the hydrolysed casein product comprises 50-200 mmol/kg $K^+$ and/or 15-60 mmol/kg $Ca^{2+}$ and/or 6-25 mmol/kg $Mg^{2+}$ more preferably, 100-150 mmol/kg $K^+$ and/or 30-50 mmol/kg $Ca^{2+}$ and/or 10-25 mmol/kg $Mg^{2+}$ and most preferably 110-135 mmol/kg $K^+$ and/or 35-45 mmol/kg $Ca^{2+}$ and/or 13-20 mmol/kg $Mg^{2+}$. The addition of these ions will have and anti-hypertensive effect.

Humans may consume the hydrolysed casein product, or products derived therefrom, as such. They may also be used in a food product as a food ingredient. Preferably, in such case the levels of equivalent IPP concentration and $K^+$, $Ca^{2+}$ and $Mg^{2+}$ of the food product are within the ranges as defined herein for the hydrolysed casein product.

The hydrolysed casein product according to the invention or food products derived therefrom may be pasteurised or sterilised.

The food products according to the invention may be of any food type. They may comprise common food ingredients in addition to the hydrolysed casein product, such as flavour, sugar, fruits, minerals, vitamins, stabilisers, thickeners, etc. in appropriate amounts. Preferably the food products are fruit juice products, dairy type products or frozen confectionary products. These preferred types of food products are described in some detail below and in the examples.

Fruit Juice Products

Examples of fruit juice products according to the invention are juices derived from citrus fruit like orange and grapefruit, tropical fruits, banana, peach, peer, strawberry, wherein the solids are partly or fully consisting of hydrolysed casein solids.

Dairy Type Products

Examples of dairy products according to the invention are milk, dairy spreads, cream cheese, milk type drinks and yoghurt, wherein the milk solids are partly or fully consisting of hydrolysed casein solids. The hydrolysed casein product may be used as such as a milk type drink. Alternatively flavour or other additives may be added. A dairy type product may also be made by adding hydrolysed casein solids to water or to a dairy product.

An example of a composition for a yoghurt type product is about 50-80 wt. % water, 0.1-15 wt. % hydrolysed casein solids, 0-15 wt. % whey powder, 0-15 wt. % sugar (e.g. sucrose), 0.01-1 wt. % yoghurt culture, 0-20 wt. % fruit, 0.05-5 wt. % vitamins and minerals, 0-2 wt. % flavour, 0-5 wt. % stabilizer (thickener or gelling agent).

A typical serving size for a yoghurt type product could be from 50 to 250 g, generally from 80 to 200 g.

Frozen Confectionery Products

For the purpose of the invention the term frozen confectionery product includes milk containing frozen confections such as ice-cream, frozen yoghurt, sherbet, sorbet, ice milk and frozen custard, water-ices, granitas and frozen fruit purees.

Preferably the level of solids in the frozen confection (e.g. sugar, fat, flavouring etc) is more than 3 wt. %, more preferred from 10 to 70 wt. %, for example 40 to 70 wt. %.

Ice cream will typically comprise 0 to 20 wt. % of fat, 0.1 to 20 wt. % hydrolysed casein solids, sweeteners, 0 to 10 wt. % of non-fat milk components and optional components such as emulsifiers, stabilisers, preservatives, flavouring ingredients, vitamins, minerals, etc, the balance being water. Typically ice cream will be aerated e.g. to an overrun of 20 to 400%, more specific 40 to 200% and frozen to a temperature of from −2 to −200° C., more specific −10 to −30° C. Ice cream normally comprises calcium at a level of about 0.1 wt %.

Other food product according to the invention can be prepared by the skilled person based on common general knowledge, using hydrolysed casein or hydrolysed casein derived products, such as hydrolysed casein solids as an ingredient in suitable amounts. Examples of such food products are baked goods, dairy type foods, snacks, etc.

Advantageously the food product is an oil and water containing emulsion, for instance a spread. Oil and water emulsion is herein defined as an emulsion comprising oil and water and includes oil in water (O/W) emulsions and water in oil emulsions (W/O) and more complex emulsions for instance water-in-oil-in-water (W/O/W/O/W) emulsions. Oil is herein defined as including fat.

Preferably the food product is a spread, frozen confection, or sauce.

Preferably a spread according to the invention comprises 30-90 wt. % vegetable oil. Advantageously a spread has a pH of 4.2-6.0.

EXAMPLES

Determination of Amounts of IPP, IPPL (SEQ ID NO: 1), LPP and VPP

Quantification of IPP, IPPL (SEQ ID NO: 1), LPP and VPP was performed using HPLC-MRM-MS in positive ESI mode. The samples were analysed using a HP1100 (ex Agilent) HPLC system combined with a Quattro-II triple quadrupole mass spectrometer (ex Micromass UK). The samples were injected on a Varian 150×2.1 mm Inertsil ODS-3 column prepacked by GL_Sciences. The eluent gradient was linear from 100% water containing 0.1% trifluoric acid (TFA) to 100% of acetonitrile containing 0.1% of TFA in 46 minutes with a flow rate of 0.2 ml/min at a column temperature of 60° C. The ion source of the MS was operating in positive-electrospray mode. The product ions m/z 213.1 and m/z 183.1 were monitored in MRM of the precursor ion m/z 326.3 for IPP and LPP, m/z 213.1 and m/z 169.1 for VPP and m/z 213.1 and m/z 189.1 for the internal standard UC13IPP. The cone voltage and collision energy was 20 V and 20 eV for all compounds. The collision gas used was Argon, and the collision gas pressure was 2.3×10-3 mbar. The quantification was performed using a separate relative internal calibration curve for both compounds.

Proteinase Activity:

Proteinase activity of the enzyme mixtures was determined using a Universal Protease Casein resorufin-labeled (ex Boehringer Mannheim) as a substrate. This assay is based on the principle resorufin-labeled peptides are released over time by degradation of the resorufin labeled casein using proteinases.

A 50 μL labeled substrate solution, a 50 μL 100 mM sodium phosphate buffer of pH 7.0 and 100 μL of enzyme solution in the appropriate dilution were mixed and incubated at 50° C. for 60 minutes. The remaining resorufin labeled casein was precipitated by addition of tricloroacetic acid and centrifugation (14000 rpm for 10 minutes). An 80 μL sample of the supernatant was added to 120 μL assay buffer (pH 8.8) and absorbance was read at 574 nm.

Several dilutions of one enzyme mixture were tested in this manner to establish a linear curve between the formed absorbance at 574 nm after 60 minutes incubation and the amount of enzyme mixture (μg). The proteinase activity was expressed in arbitrary units (AU), which was calculated by multiplying the slope of the linear curve by 10000. The specific proteinase activity was expressed as arbitrary units per μg enzyme mixture (AU/μg).

X-Prolyl Dipeptidyl Aminopeptidase Activity:

The X-prolyl dipeptidyl amino activity of the enzyme mixtures was measured using a 1 mM Glycine-Proline-para Nitroaniline (GP-pNa) substrate solution in a 100 mM sodium phosphate buffer at pH 7.0 by incubating enzyme samples in an appropriate dilution at 50° C. and monitoring the absorbance at 405 nm for 20 minutes. The enzyme activity was calculated in units from the increase of absorbance using the molar extinction coefficient of para-nitroaniline which is 9620 $M^{-1}$ $cm^{-1}$. The X-prolyl dipeptidyl amino activity is expressed as U/kg. The conversion of 1 μMol GP-pNa per min by the crude enzyme mixture represents 1 U.

Proteolytic Activity:

The presence of the total amount of amino groups, as free amino acids, peptides and proteins in hydrolysed casein samples is used to evaluate the total proteolysis after enzymatic hydrolysis and/or fermentation using lactic acid bacteria. A method to determine a degree of hydrolysis in food protein hydrolysates described by Adler-Nissen J. in Agric. Food Chem. 27, 1256-1262 (1979) was used.

A volume of 5 μL sample, 5 μL leucine standard (0.25-2.5 mM) or 5 μL demineralised water were added to 40 μL of 0.21 M phosphate buffer pH 8.2 and 40 μL of 0.1 wt % TNBS solution, followed by incubation in the dark for 60 minutes at 50° C. The reaction is quenched by adding 80 μL of 0.1 M HCl. Absorbance was measured at 340 nm (Adler-Nissen J. Enzymatic hydrolysis of food proteins. New York: Elsevier Applied Science Publishers p. 110-169 (1986)).

The total amount of amino groups present in the hydrolysed casein products was expressed as mM Leucine equivalents.

The extent of the proteolysis in the enzymatic hydrolysed and/or fermented casein products is presented as degree of hydrolysis (DH), which is defined as follows:

Degree of hydrolysis=number of peptide bonds cleaved/total number of peptide bonds present in protein*100%

Examples 1 and 2

Preparation of Hydrolysed Milk

Skimmed milk (9% SMP) was reconstituted by mixing 9 wt % skim milk powder (Promex, ex Coberco, Netherlands) in tap water and sterilised. The sterile reconstituted skim milk was incubated at 50° C. for 6 hours at pH 7.0 with either 0.16 wt % (5 wt % based on casein) Fungal Protease Concentrate (ex Genencor) or 0.16 wt % (5 wt % based on casein) Umamizyme (ex Amano). Both enzyme mixtures are derived from *Aspergillus oryzae*, and are comprised of proteinases and peptidases.

Examples 3-6 and Comparative Examples A-I

Preparation of Hydrolysed Fermented Milk

A casein starting material was fermented with *Lactobacillus helveticus* CNRZ 244 and the resulting fermented milk herein also designated as fermented milk substrate was treated with enzymes mentioned in table 1.

Preparation of the Fermented Milk Substrate:

Sterile skim milk (Yopper ex Campina, Netherlands) was inoculated for 24 hours at 37° C. with 4% of a culture of a *Lactobacillus helveticus* CNRZ 244 that had been stored at −80° C. as a full grown culture in the above described skim milk, diluted with sterile 10% glycerol to an end concentration of 6% glycerol. This preculture was designated as preculture-1

A preculture (preculture-2) was prepared with sterile skim milk (Yopper, ex Campina, Netherlands), which was inoculated with 2 wt % preculture-1 of *Lactobacillus helveticus* CNRZ 244. Preculture-2 was stirred and incubated at 40° C. for 24 hours under anaerobic conditions, using a headspace nitrogen gas flush.

Skimmed milk was reconstituted by mixing 9 wt % skim milk powder (Promex, ex Coberco, Netherlands) in tap water and sterilised. The sterile reconstituted milk was inoculated with 2 wt % of preculture-2 in a stirred tank reactor. Stirred speed was maintained at 150 rpm and dissolved oxygen and pH were monitored.

Anaerobic conditions were maintained using a headspace flush with nitrogen gas. During the first 8 hours of fermentation the pH of the milk was allowed to decrease from pH 6.5 to pH 4.6. At pH 4.6 the pH was controlled for 3.5 hours, using a base mixture of calciumhydroxide and potassiumhydroxide. After this pH controlled phase the pH was again allowed to decrease to 4.0.

After fermentation the fermented milk was pasteurised for 15 seconds at 75° C. The pasteurised fermented milk product is designated as fermented milk substrate in comparative example A.

For examples 3-6 and comparative examples B-I the fermented milk substrate was incubated with 0.16 wt % (5 wt % based on casein) of the various enzyme mixtures comprising of proteinases and peptidases at 50° C. for six hours at pH 7.

TABLE 1

Enzyme mixtures (protease and peptidase mixtures) used in examples 1-5 and comparative experiments A-K, and their activities measured in the crude enzyme mixtures.

| Example/ Comparative Experiment | Enzyme | Derived from: | Supplier | Proteolytic activity (U/kg) | X-prolyl dipeptidyl amino peptidase activity (U/kg) |
|---|---|---|---|---|---|
| 1 | Fungal protease Concentrate | *Aspergillus oryzae* | Genencor | 1219 | 730 |
| 2 | Umamizyme | *Aspergillus oryzae* | Amano | 2112 | 2768 |
| A | NA | Lb. *helveticus* Fermentation | NA | NA | NA |
| B | Proleather FG-F | *Bacillus subtilis* | Amano | 2618 | 107 |
| C | Multifect P-3000 | *Bacillus subtilis* | Genencor | 2547 | 23 |
| D | Multifect Neutral | *Bacillus amyloliquefaciens* | | 1603 | 26 |
| E | Peptidase R | *Rhizopus oryzae* | Amano | ND | ND |
| F | Protex 6L | *Bacillus licheniformis* | Genencor | 4287 | 13 |
| G | Promod 280P | *Bacillus subtilis* | Biocatalyst | ND | ND |
| H | Pepsin P389P | Hog stomach | Biocatalyst | BDL | 0 |
| I | GC 106 | *Aspergillus niger* | Genencor | BDL | 13 |
| 3 | Promod 194P | *Aspergillus* | Biocatalyst | 1025 | 483 |
| 4 | Fungal protease concentrate | *Aspergillus oryzae* | Genencor | 1219 | 730 |

TABLE 1-continued

Enzyme mixtures (protease and peptidase mixtures) used in examples 1-5 and comparative experiments A-K, and their activities measured in the crude enzyme mixtures.

| Example/ Comparative Experiment | Enzyme | Derived from: | Supplier | Proteolytic activity (U/kg) | X-prolyl dipeptidyl amino peptidase activity (U/kg) |
|---|---|---|---|---|---|
| 5 | Umamizyme | Aspergillus oryzae | Amano | 2112 | 2768 |
| K | Flavourzyme | Aspergillus oryzae | Novozymes | 357 | 117 |

(ND = not determined, NA = not applicable, BDL = below detection limit)

TABLE 2

Results of incubation experiments with protease and peptidase mixtures in examples 1-5 and comparative examples A-I

| Ex | Substrate | Conc IPPL (μM) | Conc VPP (μM) | Conc IPP (μM) | Conc LPP (μM) | IPPeq (μM) | BPPeq (μM) | Molar Yield VPP on beta-casein | Molar Yield IPP on Beta- & Kappa Casein | Molar Yield LPP on Beta-casein | Degree of Hydrolysis DH |
|---|---|---|---|---|---|---|---|---|---|---|---|
| 1 | 9% SMP | 2 | 293 | 331 | 207 | 493 | 601 | 67% | 53% | 47% | 39% |
| 2 | 9% SMP | 0 | 350 | 413 | 367 | 608 | 799 | 80% | 66% | 84% | 55% |
| A | 9% SMP | 23 | 96 | 83 | 0 | 136 | 136 | 22% | 13% | 0% | ND |
| B | Fermented milk | 13 | 49 | 40 | 0 | 67 | 67 | 11% | 6% | 0% | 19% |
| C | Fermented milk | 13 | 56 | 40 | 0 | 71 | 71 | 13% | 6% | 0% | 14% |
| D | Fermented milk | 33 | 44 | 58 | 0 | 82 | 82 | 10% | 9% | 0% | 19% |
| E | Fermented milk | 25 | 45 | 62 | 0 | 87 | 87 | 10% | 10% | 0% | 23% |
| F | Fermented milk | 14 | 89 | 38 | 0 | 87 | 87 | 20% | 6% | 0% | 15% |
| G | Fermented milk | 17 | 81 | 76 | 0 | 121 | 121 | 19% | 12% | 0% | 6% |
| H | Fermented milk | 26 | 91 | 85 | 0 | 135 | 135 | 21% | 13% | 0% | 3% |
| I | Fermented milk | 0 | 90 | 87 | 54 | 137 | 165 | 21% | 14% | 12% | 3% |
| 3 | Fermented milk | 3 | 88 | 99 | 88 | 148 | 194 | 20% | 16% | 20% | 28% |
| 4 | Fermented milk | 0 | 427 | 421 | 285 | 658 | 807 | 98% | 67% | 65% | 37% |
| 5 | Fermented milk | 0 | 320 | 354 | 375 | 532 | 727 | 73% | 56% | 86% | 52% |

(ND is Not determined; NA is Not applicable):

Results from examples 1-5 show both milk and fermented milk incubated with enzyme mixtures derived from *Aspergillus* and more in particular *Aspergillus oryzae* give rise to high IPP, LPP and VPP levels.

The molar yield of LPP on beta-casein was found to be higher than 20% in examples 1 to 5.

Examples 1, 2, 4 and 5 all show high levels of IPP, VPP and LPP and thus high corresponding IPPeq and BPPeq values were determined. In these examples the enzyme was derived from *Aspergillus Oryzae*.

Example 2 shows high levels of IPP, LPP and VPP can be obtained by incubation reconstituted milk with Umamizyme (ex Amano). Furthermore high molar yields of VPP and LPP of 80% and 84% respectively were found in example 2.

A near to complete release of all the VPP present in the beta-casein—indicated by the 98% molar yield—could be shown after the incubation of fermented milk with Fungal protease concentrate (ex Genencor) in example 4.

The high values for total proteolysis in examples 1, 2, 4 and 5 correspond to a high degree of hydrolysis of 37 to 55% of the milk proteins.

In examples 1-5 very low or no presence of IPPL was found. During these incubations most of the IPPL formed therefore converted into IPP.

The comparative examples B-H showed a decrease in concentration of the bio-active peptides IPP and VPP after incubation with the proteinase and peptidase mixtures, compared to the concentrations present in the fermented milk substrate (example A). No formation of LPP could be shown in these comparative examples B to H.

Examples 6 and 7

Preparation of Milk and Fermented Milk Drinks

The hydrolysed casein products obtained according to examples 1 and 4 were used to produce milk and fermented milk drinks.

The milk drinks contained 12.5 wt % of hydrolysed casein products in pasteurised skim milk and the following ingredients: 4.5 wt % sucrose (ex CSM, Netherlands), 1 wt % fructose syrup (ex Sensus, Netherlands), 2 wt % Multifruit fruit-pulp (ex Wild, Netherlands), 0.1 wt % yoghurt flavour ZD-49492 (ex Quest, Netherlands), 0.03 wt % fruit flavour 037-00330-11 (ex Givaudan, Switzerland), 0.1 wt % cream flavour U33162 (ex Danisco, Denmark) and 0.8 wt. % Genu pectine YM-115-H (ex CP Kelco, Denmark).

After the ingredients were mixed in, the milk drinks were homogenised at 150 bar and pasteurised for 15 seconds at 75° C.

The taste of the milk drinks was good. No bitterness was noticed.

Example 8

Preparation of a Yoghurt Drink Containing Hydrolysed Casein Solids

The hydrolysed casein solids was prepared as described herein:

A reactor was filled with 10 wt % calcium caseinate (ex DMV, Netherlands), pasteurised at 85° C. for 20 minutes, cooled to 50° C. and incubated under anaerobic conditions with 0.5% wt Umamizyme (ex Amano) for 6 hours at 50° C.

After incubation the pH of the hydrolysate was adjusted from pH 6.2 to pH 4 using 80% wt lactic acid (ex Purac, Netherlands) and the remaining enzymes were deactivated by heating the hydrolysate at 95° C. for 20 minutes. Prior to freeze drying the hydrolysate was stored at −20° C.

After freeze drying the content of the tripeptides VPP, IPP and LPP were analysed by HPLC-MRM-MS as described before. The hydrolysed casein solids contained:

1677.2 µg/g VPP; 2664.6 µg/g IPP and 2019.5 µg/g LPP (averaged values from six measurements).

The yoghurt drink contained 60 wt % low fat yoghurt (ex Melkan, Netherlands); 9 wt % sucrose (ex CSM, Netherlands); 0.35 wt % AMD 783 pectine (ex Danisco, Denmark); 1.23 wt % hydrolysed casein solids; 0.025 wt % raspberry 502824 A (ex Firmenich, Switserland) and 29.4 wt % demineralised water.

After all ingredients were mixed into the yoghurt the yoghurt drink was homogenised at 150 bar and pasteurised for 15 seconds at 75° C.

The final VPP, IPP and LPP content of the yoghurt drink was 66 µM, 100 µM and 76 µM respectively. The taste of the yoghurt drink containing 1.23 wt % hydrolysed casein solids was good and no bitter taste was noticed.

Examples 9-12

Preparation of Hydrolysed Casein and Reconstituted Milk using Different Levels of Casein and Skim Milk Powder The 3.2 wt %; 6 wt % and 10 wt % casein substrates were prepared by mixing in appropriate levels of calcium caseinate (ex DMV, Netherlands) in tap water. A high skim milk (18% SMP) substrate was prepared by mixing 18 wt % skim milk powder (ex Coberco, Netherlands) in tap water. All substrates, 18% SMP and the casein substrates were incubated at 50° C. for six hours. Prior to these incubations the pH was adjusted to pH 7.0. All substrates were incubated with Umamizyme (ex Amano), the ratio enzyme mixture to casein was 5 wt %.

TABLE 3

Results of the incubation experiments using Umamizyme at different levels of casein and skim milk powder in examples 9-12.

| Ex. | Substrate | Conc VPP (µM) | Conc IPP (µM) | Conc LPP (µM) | IPPeq (µM) | BPPeq (µM) | Molar yield VPP on beta-casein | Molar yield IPP on beta- & kappa casein | Molar yield LPP on beta-casein | Degree of Hydrolysis DH |
|---|---|---|---|---|---|---|---|---|---|---|
| 9 | 3.2% casein | 294 | 417 | 343 | 580 | 758 | 67% | 66% | 78% | 59% |
| 10 | 6.0% casein | 473 | 732 | 566 | 995 | 1289 | 58% | 62% | 69% | 55% |
| 11 | 10.0% casein | 703 | 1000 | 794 | 1391 | 1804 | 51% | 51% | 58% | 57% |
| 12 | 18% SMP | 541 | 628 | 522 | 929 | 1201 | 62% | 50% | 60% | 46% |

Results from examples 9, 10 and 11 clearly show increased amounts of casein substrate lead to higher levels of the bioactive peptides VPP, IPP and LPP and to very high corresponding IPPeq and BPPeq values. With increasing casein substrate levels the molar yields of VPP, IPP and LPP on casein decreased although the resulting molar yields at the highest level of casein substrate (10 wt %) are still above 50%.

Examples 13-15 and Comparative Example J

Preparation of Hydrolysed Casein using Different Enzyme/Substrate Ratios

The substrate used in these incubations contained 10 wt % casein and was prepared by mixing an appropriate level of calcium caseinate (ex DMV, Netherlands) in tap water. The incubation was performed at 50° C. for six hours and prior to these incubations the pH was not adjusted. All incubation were performed using the Umamizyme (ex Amano) enzyme mixture, the ratio enzyme mixture to casein used were 1 wt %; 2.5 wt %; 4 wt % and 5 wt %.

TABLE 4

Results of the incubation experiments using different enzyme/substrate ratios in examples 13-15 and comparative example J.

| Ex. | Enzyme/ Substrate Ratio | Conc VPP (μM) | Conc IPP (μM) | Conc LPP (μM) | IPPeq (μM) | BPPeq (μM) | Molar yield VPP on beta-casein | Molar yield IPP on beta- & kappa casein | Molar yield LPP on beta-casein | Degree of hydrolysis DH |
|---|---|---|---|---|---|---|---|---|---|---|
| J | 1.0% | 84 | 166 | 72 | 213 | 250 | 6% | 8% | 5% | 29% |
| 13 | 2.5% | 398 | 730 | 543 | 951 | 1234 | 29% | 37% | 40% | 42% |
| 14 | 4.0% | 727 | 1005 | 810 | 1409 | 1831 | 53% | 51% | 59% | 47% |
| 15 | 5.0% | 986 | 983 | 814 | 1531 | 1955 | 72% | 50% | 59% | 52% |

Results from example 13-15 and comparative example J indicate an enzyme to substrate ratio over 1% is needed to obtain high yields of VPP, IPP and LPP on the casein substrate.

Again very high levels of VPP, IPP and LPP were obtained. In example 15 the highest levels VPP, IPP and LPP were obtained corresponding to an IPPeq value of 1531 μM and a BPPeq value of 1955 μM.

Comparative Example K

Preparation of Hydrolysed Casein using Flavourzyme

Comparative example K was executed according to example 15 with an enzyme to substrate ratio of 5% based on casein, except in this case a different enzyme mixture is used. A 10% casein solution was incubated using Flavourzyme (ex Novozymes) instead of Umamizyme (ex Amano). After the incubation the bioactive peptide VPP and the degree of hydrolysis were determined. Some characteristics of the Flavourzyme enzyme mixture are shown in Table 1.

TABLE 5

Results incubation experiment of 10% casein using Flavourzyme

| Example | Substrate | Enzyme/ Substrate ratio | Conc VPP (μM) | Molar yield VPP on beta-casein | Degree Of Hydrolysis DH |
|---|---|---|---|---|---|
| K | 10% casein | 5% | 16 | 1% | 45% |

Results indicate besides a high proteolytic activity a relatively high X-prolyl dipeptidyl amino peptidase activity is needed to obtain high levels of the active tripeptide VPP.

The invention claimed is:

1. A hydrolyzed casein food product comprising the Ile-Pro-Pro (IPP), Leu-Pro-Pro (LPP) and Val-Pro-Pro (VPP),
   a) wherein the IPP-equivalent concentration (IPPeq) is 400 μM or more, said IPPeq consisting of concentrations of said IPP ([IPP]) and VPP ([VPP]), wherein said IPPeq=[IPP]+5/9 [VPP] expressed in μM;
   b) wherein the BPP-equivalent concentration (BPPeq) is at least 500 μM said BPPeq consisting of said [IPP], said [VPP], and a concentration of said LPP ([LPP]), wherein said BPPeq=[IPP]+5/9 [VPP]+5/9.6 [LPP] expressed in μM; and
   c) wherein the food product has a non-bitter taste.

2. The hydrolyzed casein food product of claim 1, wherein said food product is free from the peptide Ile-Pro-Pro-Leu (IPPL) (SEQ ID NO: 1).

3. The hydrolyzed casein food product of claim 1, further comprising an enzyme obtained from *Aspergillus oryzae*.

4. The hydrolyzed casein food product of claim 1, wherein said [LPP] is 25 μM or more.

* * * * *

SEQUENCE LISTING

<160> NUMBER OF SEQ ID NOS: 1

<210> SEQ ID NO 1
<211> LENGTH: 4
<212> TYPE: PRT
<213> ORGANISM: Artificial sequence
<220> FEATURE:
<223> OTHER INFORMATION: Milk oligopeptide

<400> SEQUENCE: 1

Ile Pro Pro Leu
1